United States Patent
Kozlov et al.

(10) Patent No.: US 10,722,602 B2
(45) Date of Patent: *Jul. 28, 2020

(54) REMOVAL OF MICROORGANISMS FROM FLUID SAMPLES USING NANOFIBER FILTRATION MEDIA

(71) Applicant: EMD Millipore Corporation, Burlington, MA (US)

(72) Inventors: Mikhail Kozlov, Burlington, MA (US); Wilson Moya, Burlington, MA (US); Gabriel Tkacik, Bedford, MA (US)

(73) Assignee: EMD MILLIPORE CORPORATION, Burlington, MA (US)

( * ) Notice: Subject to any disclaimer, the term of this patent is extended or adjusted under 35 U.S.C. 154(b) by 15 days.

This patent is subject to a terminal disclaimer.

(21) Appl. No.: 16/053,523

(22) Filed: Aug. 2, 2018

(65) Prior Publication Data
US 2019/0015533 A1   Jan. 17, 2019

Related U.S. Application Data

(63) Continuation of application No. 15/691,286, filed on Aug. 30, 2017, now Pat. No. 10,064,965, which is a
(Continued)

(51) Int. Cl.
*B01D 39/16* (2006.01)
*A61L 2/00* (2006.01)
(Continued)

(52) U.S. Cl.
CPC ........ *A61L 2/0017* (2013.01); *B01D 39/1623* (2013.01); *B01D 67/002* (2013.01);
(Continued)

(58) Field of Classification Search
CPC ............ B01D 39/1623; B01D 39/1692; B01D 39/18; B01D 2239/025; B01D 2239/065;
(Continued)

(56) References Cited

U.S. PATENT DOCUMENTS 500,167 A   6/1893   Surerus et al.
552,291 A   12/1895  Keefer
(Continued)

FOREIGN PATENT DOCUMENTS

CN   2390670 Y   8/2000
CN   1471421 A   1/2004
(Continued)

OTHER PUBLICATIONS

Aranha, "Ensuring Safety of Biopharmaceuticals: Virus and Prion Safety Considerations", Chapter 20 in "Filtration and Purification in the Biopharmaceutical Industry," eds.Meltzer et al., 2nd edition, Informa Healthcare USA, Inc., pp. 543-577 (2008).
(Continued)

*Primary Examiner* — Patrick Orme
(74) *Attorney, Agent, or Firm* — EMD Millipore Corporation

(57) ABSTRACT

A method for removing microorganisms from liquid samples and a nanofiber containing liquid filtration medium that simultaneously exhibits high liquid permeability and high microorganism retention. Microorganisms such as bacteria, particularly B. Diminuta, are removed from a liquid by passing the liquid through a porous nanofiber containing filtration medium having a B. Diminuta LRV greater than about 9, and the nanofiber(s) has a diameter from about 10 nm to about 1,000 nm. Another method for removing microorganisms such as bacteria and *Mycloplasma*, includes passing the liquid through a porous nanofiber containing filtration medium having a microorganism LRV greater than about 8, and the nanofiber(s) has a diameter from about 10 nm to about 1,000 nm. The filtration medium can be in the form of a fibrous electro spun polymeric nanofiber liquid filtration medium mat.

20 Claims, 6 Drawing Sheets

Figure 1:
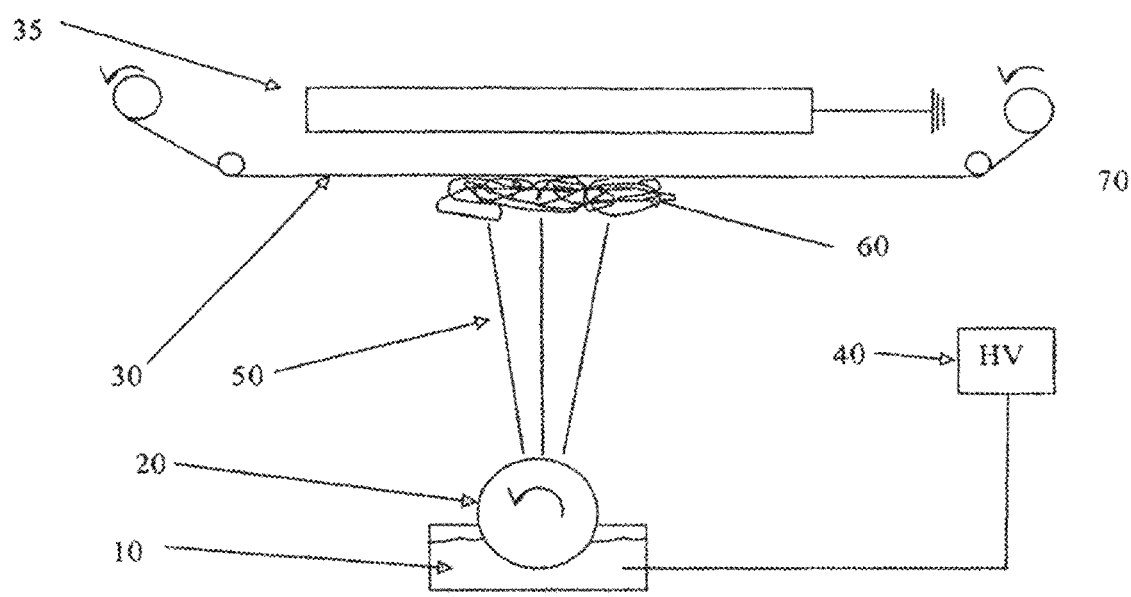
Figure 2:
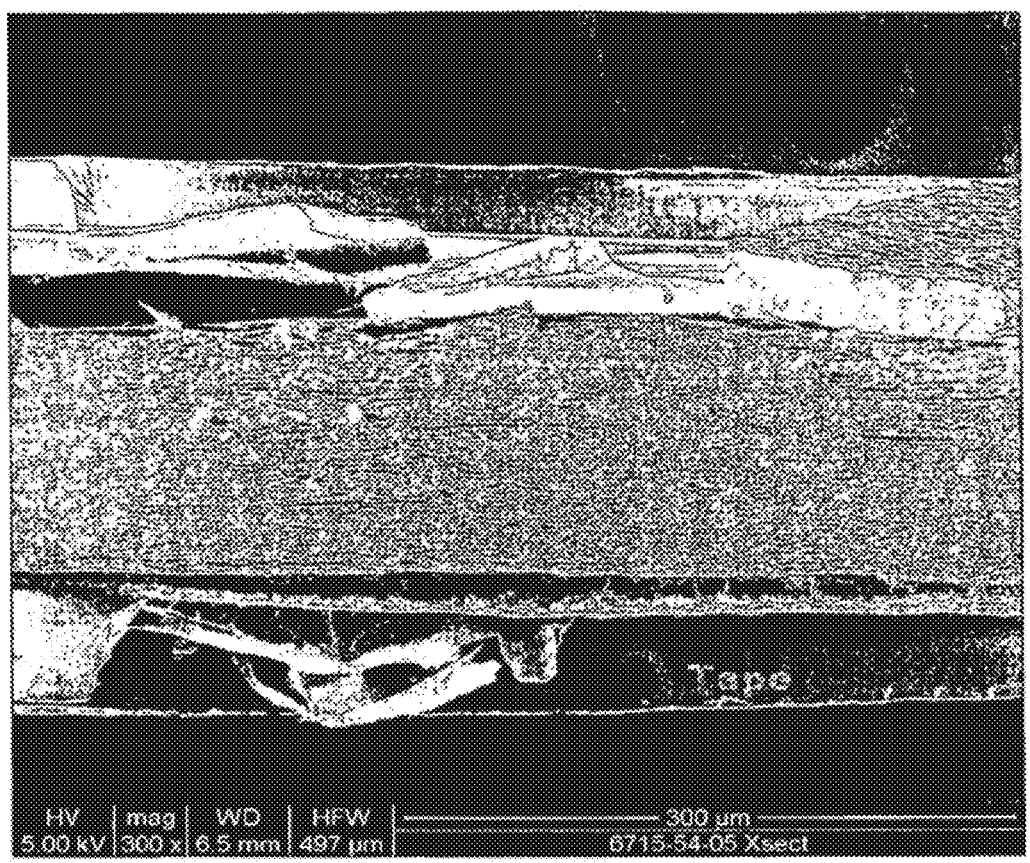
Figure 3:
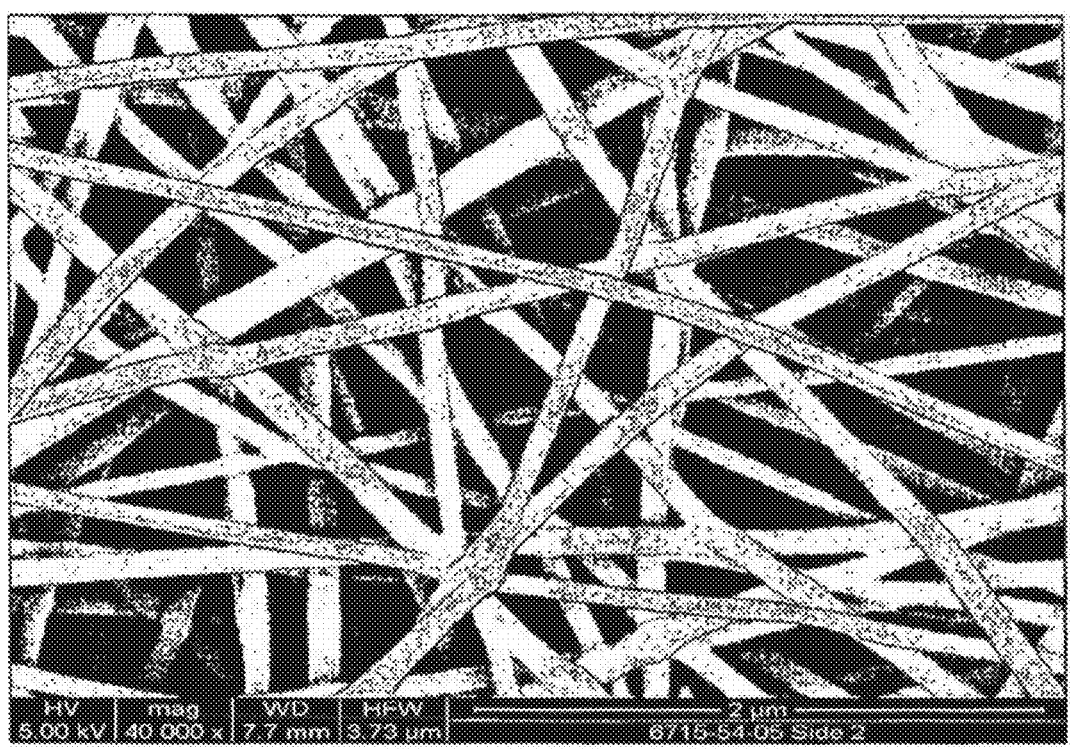
Figure 4:
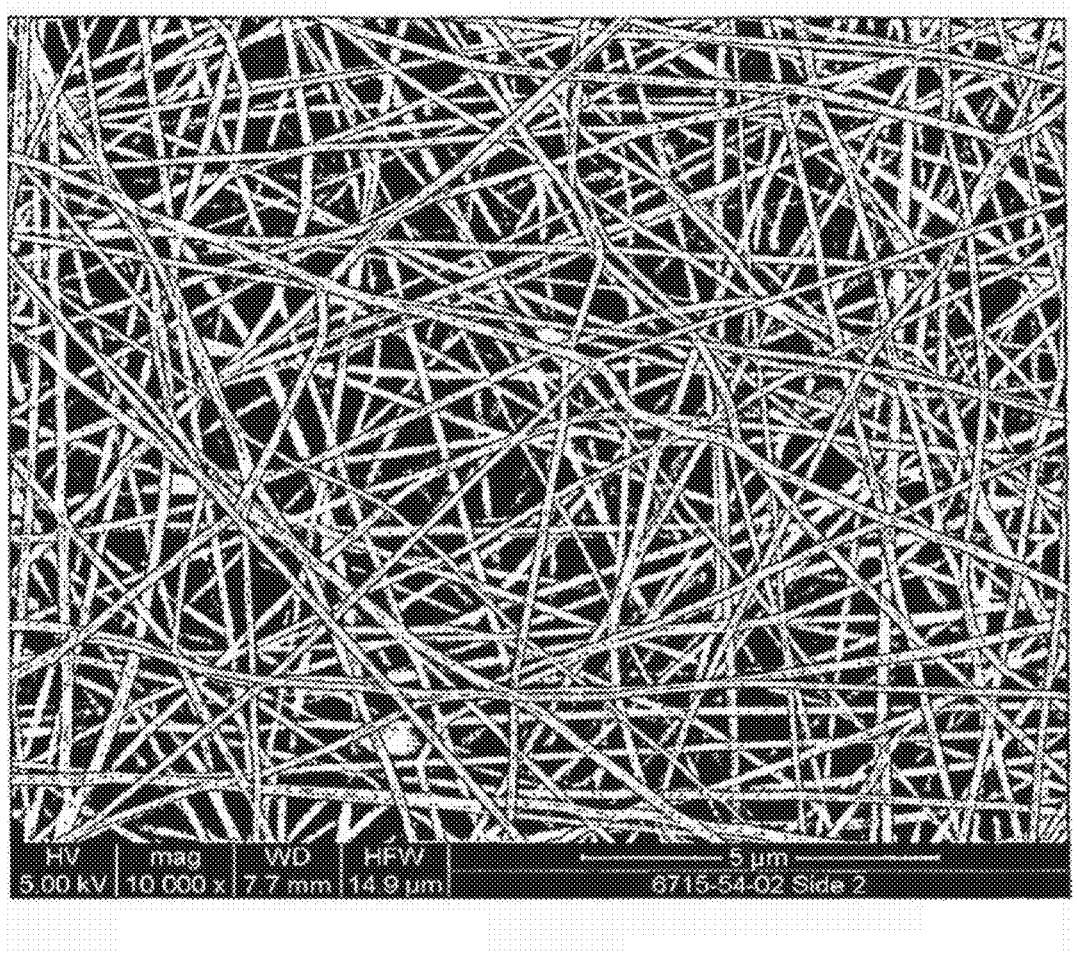
Figure 5:
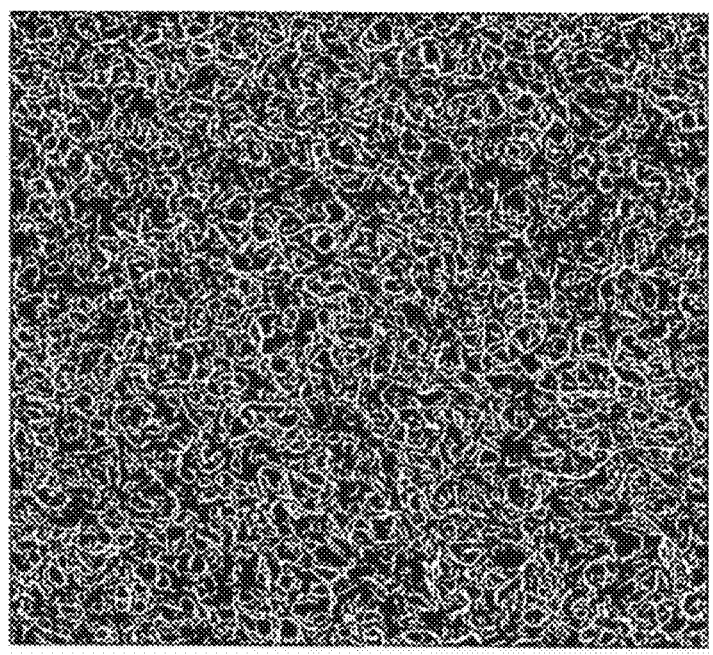
Figure 6:
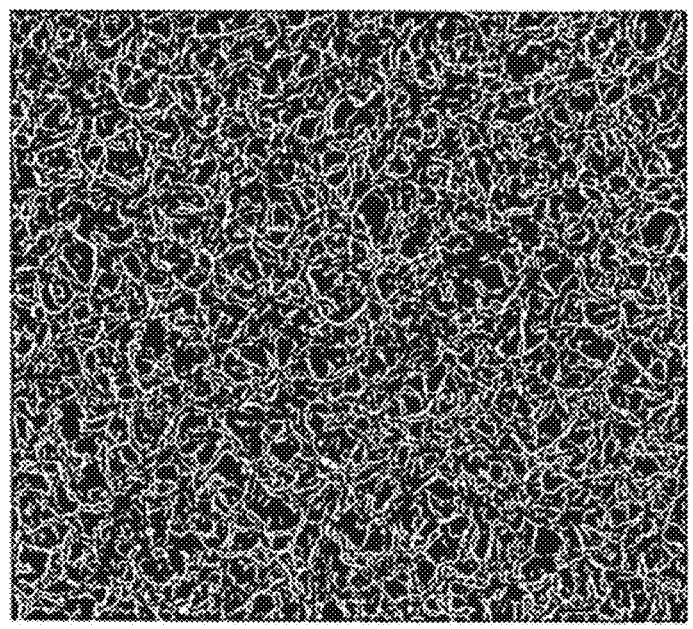

Related U.S. Application Data continuation of application No. 13/257,501, filed as application No. PCT/US2010/000826 on Mar. 19, 2010, now Pat. No. 9,750,829.

(60) Provisional application No. 61/210,468, filed on Mar. 19, 2009.

(51) Int. Cl.
  *B01D 67/00* (2006.01)
  *B01D 69/00* (2006.01)
  *C02F 1/44* (2006.01)

(52) U.S. Cl.
  CPC ......... *B01D 67/0004* (2013.01); *B01D 69/00* (2013.01); *B01D 2239/025* (2013.01); *B01D 2323/39* (2013.01); *C02F 1/444* (2013.01); *C02F 2303/04* (2013.01)

(58) Field of Classification Search
  CPC ............ B01D 2323/39; B01D 2325/02; B01D 2325/028; B01D 2325/04; B01D 2325/20; B01D 2325/40; B01D 61/145; B01D 61/147; B01D 71/06; B01D 71/56; C12Q 1/22; A61L 2/0017; A61L 2/022; B01J 20/28007; B01J 20/28054; B01J 20/3295; C02F 1/288; C02F 1/444; C02F 2305/08; D01D 5/0007

See application file for complete search history.

(56) References Cited

U.S. PATENT DOCUMENTS

| | | |
|---|---|---|
| 692,631 A | 2/1902 | Cooley |
| 705,691 A | 7/1902 | Morton |
| 1,699,615 A | 1/1929 | Iwasaki |
| 1,975,504 A | 10/1934 | Formhals |
| 1,975,594 A | 10/1934 | Stroud et al. |
| 2,048,651 A | 7/1936 | Norton |
| 2,158,415 A | 5/1939 | Formhals |
| 2,158,416 A | 5/1939 | Formhals |
| 2,160,962 A | 6/1939 | Formhals |
| 2,168,027 A | 8/1939 | Gladding |
| 2,349,950 A | 5/1944 | Formhals |
| 3,585,126 A | 6/1971 | Cannon et al. |
| 3,620,970 A | 11/1971 | Klug et al. |
| 3,864,289 A | 2/1975 | Rendall |
| 3,876,738 A | 4/1975 | Marinaccio et al. |
| 3,994,258 A | 11/1976 | Simm |
| 4,043,331 A | 8/1977 | Martin et al. |
| 4,069,026 A | 1/1978 | Simm et al. |
| 4,127,706 A | 11/1978 | Martin et al. |
| 4,143,196 A | 3/1979 | Simm et al. |
| 4,261,834 A | 4/1981 | deWinter |
| 4,323,525 A | 4/1982 | Bornat |
| 4,510,047 A | 4/1985 | Thompson |
| 4,604,326 A | 8/1986 | Manabe et al. |
| 4,629,563 A | 12/1986 | Wrasidlo |
| 4,650,506 A | 3/1987 | Barris et al. |
| 4,657,793 A | 4/1987 | Fisher et al. |
| 4,704,324 A | 11/1987 | Davis et al. |
| 4,778,601 A | 10/1988 | Lopatin et al. |
| 4,824,568 A | 4/1989 | Allegrezza, Jr. et al. |
| 4,839,203 A | 6/1989 | Davis et al. |
| 4,853,129 A | 8/1989 | Wan |
| 4,938,869 A | 7/1990 | Bayerlein et al. |
| 4,983,268 A | 1/1991 | Kirkpatrick et al. |
| 4,983,288 A | 1/1991 | Karbachsch et al. |
| 5,096,473 A | 3/1992 | Sassa et al. |
| 5,228,994 A | 7/1993 | Tkacik et al. |
| 5,238,106 A | 8/1993 | Nguyen et al. |
| 5,238,568 A | 8/1993 | Fely et al. |
| 5,264,165 A | 11/1993 | Knight |
| 5,500,167 A | 3/1996 | Degen |
| 5,507,847 A | 4/1996 | George et al. |
| 5,522,601 A | 6/1996 | Murphy |
| 5,522,991 A | 6/1996 | Tuccelli et al. |
| 5,536,413 A | 7/1996 | Bormann et al. |
| 5,620,790 A | 4/1997 | Holzki et al. |
| 5,652,050 A | 7/1997 | Pall et al. |
| 5,693,231 A | 12/1997 | Johnson et al. |
| 5,731,164 A | 3/1998 | Becker et al. |
| 5,739,316 A | 4/1998 | Beer et al. |
| 5,846,438 A | 12/1998 | Pall et al. |
| 5,968,650 A | 10/1999 | Tennent et al. |
| 5,985,112 A | 11/1999 | Fischer |
| 6,045,899 A | 4/2000 | Wang et al. |
| 6,074,869 A | 6/2000 | Pall et al. |
| 6,113,794 A | 9/2000 | Kumar et al. |
| 6,143,675 A | 11/2000 | McCollam et al. |
| 6,153,098 A | 11/2000 | Bayerlein et al. |
| 6,315,805 B1 | 11/2001 | Strauss |
| 6,321,915 B1 | 11/2001 | Wilson et al. |
| 6,464,881 B2 | 10/2002 | Thoraval |
| 6,513,666 B2 | 2/2003 | Meyering et al. |
| 6,554,881 B1 | 4/2003 | Healey |
| 6,598,749 B2 | 7/2003 | Paul et al. |
| 6,604,925 B1 | 8/2003 | Dubson |
| 6,713,011 B2 | 3/2004 | Chu et al. |
| 6,743,273 B2 | 6/2004 | Chung et al. |
| 6,746,517 B2 | 6/2004 | Benson et al. |
| 6,770,204 B1 | 8/2004 | Koslow |
| 6,796,169 B2 | 9/2004 | Makino et al. |
| 6,797,169 B2 | 9/2004 | Ide et al. |
| 6,835,311 B2 | 12/2004 | Koslow |
| 6,858,057 B2 | 2/2005 | Healey |
| 6,866,704 B2 | 3/2005 | Koslow |
| 6,866,794 B1 | 3/2005 | Zhang et al. |
| 6,872,311 B2 | 3/2005 | Koslow |
| 6,913,154 B2 | 7/2005 | Koslow |
| 6,924,028 B2 | 8/2005 | Chung et al. |
| 6,953,604 B2 | 10/2005 | Koslow |
| 6,955,775 B2 | 10/2005 | Chung et al. |
| 6,959,820 B2 | 11/2005 | Koslow |
| 6,974,490 B2 | 12/2005 | Gillingham et al. |
| 6,994,811 B2 | 2/2006 | Kools |
| 6,998,058 B2 | 2/2006 | Koslow |
| 7,008,465 B2 | 3/2006 | Graham et al. |
| 7,008,537 B2 | 3/2006 | Koslow |
| 7,070,640 B2 | 7/2006 | Chung et al. |
| 7,070,836 B2 | 7/2006 | Czado |
| 7,090,712 B2 | 8/2006 | Gillingham et al. |
| 7,090,715 B2 | 8/2006 | Chung et al. |
| 7,097,694 B1 | 8/2006 | Jaroszczyk et al. |
| 7,105,228 B2 | 9/2006 | Averdung et al. |
| 7,108,791 B2 | 9/2006 | Tkacik et al. |
| 7,109,136 B2 | 9/2006 | Senecal et al. |
| 7,115,150 B2 | 10/2006 | Johnson et al. |
| 7,144,533 B2 | 12/2006 | Koslow |
| 7,179,317 B2 | 2/2007 | Chung et al. |
| 7,229,665 B2 | 6/2007 | Kools |
| 7,235,122 B2 | 6/2007 | Bryner et al. |
| 7,270,692 B2 | 9/2007 | Gillingham et al. |
| 7,270,693 B2 | 9/2007 | Chung et al. |
| 7,318,853 B2 | 1/2008 | Chung et al. |
| 7,378,020 B2 | 5/2008 | Ieraci et al. |
| 7,419,601 B2 | 9/2008 | Cooper et al. |
| 7,459,085 B2 | 12/2008 | Koguma et al. |
| 7,470,639 B2 | 12/2008 | Angelini et al. |
| 7,555,195 B2 | 6/2009 | Yamashita et al. |
| 7,585,437 B2 | 9/2009 | Jirsak et al. |
| 7,743,929 B2 | 6/2010 | Kools |
| 7,789,930 B2 | 9/2010 | Ensor et al. |
| 7,790,135 B2 | 9/2010 | Lennhoff |
| 7,875,380 B2 | 1/2011 | Chun et al. |
| 7,927,885 B2 | 4/2011 | Nishita |
| 7,993,523 B2 | 8/2011 | Chen et al. |
| 8,038,013 B2 | 10/2011 | Chen et al. |
| 8,222,166 B2 | 7/2012 | Chu et al. |
| 8,282,712 B2 | 10/2012 | Chi et al. |
| 8,361,180 B2 | 1/2013 | Lim et al. |
| 8,366,797 B2 | 2/2013 | Chung et al. |
| 8,679,217 B2 | 3/2014 | Chi et al. |

(56) References Cited

U.S. PATENT DOCUMENTS

| | | | |
|---|---|---|---|
| 8,689,985 B2 | 4/2014 | Bates, III et al. | |
| 9,174,152 B2 | 11/2015 | Dai et al. | |
| 9,180,393 B2 | 11/2015 | Chen et al. | |
| 9,623,352 B2 | 4/2017 | Kas et al. | |
| 9,750,829 B2 | 9/2017 | Kozlov et al. | |
| 9,889,214 B2 | 2/2018 | Kozlov et al. | |
| 9,943,616 B2 | 4/2018 | Kozlov et al. | |
| 10,064,965 B2 | 9/2018 | Kozlov et al. | |
| 2002/0046656 A1 | 4/2002 | Benson et al. | |
| 2002/0084178 A1 | 7/2002 | Dubson et al. | |
| 2002/0096246 A1 | 7/2002 | Sennet et al. | |
| 2002/0100725 A1 | 8/2002 | Lee et al. | |
| 2002/0124953 A1 | 9/2002 | Sennett et al. | |
| 2002/0175124 A1 | 11/2002 | Tkacik et al. | |
| 2003/0010002 A1 | 1/2003 | Johnson et al. | |
| 2003/0026985 A1 | 2/2003 | Greiner et al. | |
| 2003/0121844 A1 | 7/2003 | Koo et al. | |
| 2003/0137083 A1 | 7/2003 | Ko et al. | |
| 2003/0177909 A1 | 9/2003 | Koslow | |
| 2003/0213218 A1 | 11/2003 | Dubson | |
| 2003/0213744 A1 | 11/2003 | Kools et al. | |
| 2004/0017011 A1 | 1/2004 | Narita et al. | |
| 2004/0036014 A1 | 2/2004 | Simon | |
| 2004/0038013 A1 | 2/2004 | Schaefer et al. | |
| 2004/0038014 A1 | 2/2004 | Schaefer et al. | |
| 2004/0070118 A1 | 4/2004 | Czado | |
| 2004/0080083 A1 | 4/2004 | Czado | |
| 2004/0116025 A1 | 6/2004 | Gogins et al. | |
| 2004/0118770 A1 | 6/2004 | Sale et al. | |
| 2004/0159609 A1 | 8/2004 | Chase | |
| 2004/0206693 A1 | 10/2004 | Charkoudian et al. | |
| 2004/0206694 A1 | 10/2004 | Charkoudian | |
| 2004/0207126 A1 | 10/2004 | Czado | |
| 2004/0255783 A1 | 12/2004 | Graham et al. | |
| 2005/0026526 A1 | 2/2005 | Verdegan et al. | |
| 2005/0048274 A1 | 3/2005 | Rabolt et al. | |
| 2005/0051487 A1 | 3/2005 | Koslow | |
| 2005/0053782 A1 | 3/2005 | Sen et al. | |
| 2005/0067732 A1 | 3/2005 | Kim et al. | |
| 2005/0073075 A1 | 4/2005 | Chu et al. | |
| 2005/0142973 A1 | 6/2005 | Bletsos et al. | |
| 2005/0163955 A1 | 7/2005 | Schaefer et al. | |
| 2005/0210844 A1 | 9/2005 | Kahlbaugh et al. | |
| 2005/0235619 A1 | 10/2005 | Heinz et al. | |
| 2005/0247236 A1 | 11/2005 | Frey et al. | |
| 2005/0260381 A1 | 11/2005 | Ditter et al. | |
| 2005/0272925 A1 | 12/2005 | Charkoudian et al. | |
| 2006/0016748 A1 | 1/2006 | Koguma et al. | |
| 2006/0053782 A1 | 3/2006 | Kobayashi et al. | |
| 2006/0057377 A1 | 3/2006 | Harrison et al. | |
| 2006/0060519 A1 | 3/2006 | Tkacik et al. | |
| 2006/0068668 A1 | 3/2006 | Kameoka et al. | |
| 2006/0084340 A1 | 4/2006 | Bond et al. | |
| 2006/0084341 A1 | 4/2006 | Bodaghi et al. | |
| 2006/0086657 A1 | 4/2006 | Kools | |
| 2006/0094320 A1 | 5/2006 | Chen et al. | |
| 2006/0096912 A1 | 5/2006 | Nussbaumer et al. | |
| 2006/0097431 A1 | 5/2006 | Hovanec | |
| 2006/0135020 A1 | 6/2006 | Weinberg et al. | |
| 2006/0137317 A1 | 6/2006 | Bryner et al. | |
| 2006/0137318 A1 | 6/2006 | Lim et al. | |
| 2006/0138710 A1 | 6/2006 | Bryner et al. | |
| 2006/0138711 A1 | 6/2006 | Bryner et al. | |
| 2006/0144782 A1 | 7/2006 | Buck | |
| 2006/0149561 A1 | 7/2006 | Govender | |
| 2006/0151094 A1 | 7/2006 | Angelini et al. | |
| 2006/0160064 A1 | 7/2006 | Carbonell | |
| 2006/0213829 A1 | 9/2006 | Rutledge et al. | |
| 2006/0230731 A1 | 10/2006 | Kalayci et al. | |
| 2006/0246798 A1 | 11/2006 | Reneker et al. | |
| 2006/0264139 A1 | 11/2006 | Czado | |
| 2006/0264140 A1 | 11/2006 | Andrady et al. | |
| 2006/0286446 A1 | 12/2006 | Chun et al. | |
| 2006/0286886 A1 | 12/2006 | Komura et al. | |
| 2006/0290031 A1 | 12/2006 | Jirsak et al. | |
| 2006/0293116 A1 | 12/2006 | Hocknell et al. | |
| 2006/0293169 A1 | 12/2006 | Srinivasan et al. | |
| 2007/0009736 A1 | 1/2007 | Chuang et al. | |
| 2007/0018361 A1 | 1/2007 | Xu | |
| 2007/0021021 A1 | 1/2007 | Verdegan et al. | |
| 2007/0040305 A1 | 2/2007 | Armantrout et al. | |
| 2007/0042069 A1 | 2/2007 | Armantrout et al. | |
| 2007/0062855 A1 | 3/2007 | Chase et al. | |
| 2007/0074628 A1 | 4/2007 | Jones et al. | |
| 2007/0075015 A1* | 4/2007 | Bates, III | B01D 39/1623 210/505 |
| 2007/0084786 A1 | 4/2007 | Smithies | |
| 2007/0113530 A1 | 5/2007 | Morozov et al. | |
| 2007/0125700 A1 | 6/2007 | Ding et al. | |
| 2007/0134151 A1 | 6/2007 | Jo et al. | |
| 2007/0151921 A1 | 7/2007 | Nakano et al. | |
| 2007/0163217 A1 | 7/2007 | Frey et al. | |
| 2007/0175196 A1 | 8/2007 | Tepper et al. | |
| 2007/0196401 A1 | 8/2007 | Naruse et al. | |
| 2007/0240576 A1 | 10/2007 | von Blucher et al. | |
| 2007/0298072 A1 | 12/2007 | Kitazono et al. | |
| 2008/0004205 A1 | 1/2008 | Tkacik et al. | |
| 2008/0004206 A1 | 1/2008 | Rosen et al. | |
| 2008/0010959 A1 | 1/2008 | Gillingham et al. | |
| 2008/0020192 A1 | 1/2008 | Yen et al. | |
| 2008/0022024 A1 | 1/2008 | Mao | |
| 2008/0026041 A1* | 1/2008 | Tepper | B01D 39/2017 424/445 |
| 2008/0034967 A1 | 2/2008 | Ping | |
| 2008/0060328 A1 | 3/2008 | Devine | |
| 2008/0070463 A1 | 3/2008 | Arora et al. | |
| 2008/0073296 A1 | 3/2008 | Dema et al. | |
| 2008/0099398 A1 | 5/2008 | Hu et al. | |
| 2008/0110342 A1 | 5/2008 | Ensor et al. | |
| 2008/0110822 A1 | 5/2008 | Chung et al. | |
| 2008/0134652 A1 | 6/2008 | Lim et al. | |
| 2008/0136063 A1 | 6/2008 | Chuang et al. | |
| 2008/0149561 A1 | 6/2008 | Chu et al. | |
| 2008/0150192 A1 | 6/2008 | Perret et al. | |
| 2008/0150197 A1 | 6/2008 | Chang et al. | |
| 2008/0164214 A1 | 7/2008 | Lerner et al. | |
| 2008/0207076 A1 | 8/2008 | Jirsak et al. | |
| 2008/0213574 A1 | 9/2008 | McKee et al. | |
| 2008/0217239 A1 | 9/2008 | Chen et al. | |
| 2008/0217241 A1 | 9/2008 | Smithies et al. | |
| 2008/0217807 A1 | 9/2008 | Lee et al. | |
| 2008/0220241 A1 | 9/2008 | Abdelsalam et al. | |
| 2008/0237934 A1 | 10/2008 | Reneker et al. | |
| 2008/0242171 A1 | 10/2008 | Huang et al. | |
| 2008/0264258 A1 | 10/2008 | Mares et al. | |
| 2008/0264259 A1 | 10/2008 | Leung | |
| 2008/0274312 A1 | 11/2008 | Schelling et al. | |
| 2008/0284050 A1 | 11/2008 | Mares et al. | |
| 2008/0302074 A1 | 12/2008 | Gebert et al. | |
| 2009/0026137 A1 | 1/2009 | Chen et al. | |
| 2009/0065436 A1 | 3/2009 | Kalayci et al. | |
| 2009/0110873 A1 | 4/2009 | Jiang et al. | |
| 2009/0199717 A1 | 8/2009 | Green et al. | |
| 2009/0220241 A1 | 9/2009 | Katagiri et al. | |
| 2010/0096066 A1 | 4/2010 | Ramaswamy et al. | |
| 2010/0139224 A1 | 6/2010 | Lim et al. | |
| 2010/0193428 A1 | 8/2010 | Hane et al. | |
| 2010/0206803 A1 | 8/2010 | Ward et al. | |
| 2010/0316988 A1 | 12/2010 | Sehgal | |
| 2011/0163035 A1 | 7/2011 | Cheng et al. | |
| 2011/0198282 A1 | 8/2011 | Chu et al. | |
| 2011/0206973 A1 | 8/2011 | Brant et al. | |
| 2011/0233152 A1 | 9/2011 | Wieczorek et al. | |
| 2011/0266213 A1 | 11/2011 | Jo et al. | |
| 2011/0305872 A1 | 12/2011 | Li et al. | |
| 2012/0061314 A1 | 3/2012 | Choi et al. | |
| 2012/0061332 A1 | 3/2012 | Kas et al. | |
| 2012/0091072 A1 | 4/2012 | Kozlov et al. | |
| 2012/0125847 A1 | 5/2012 | Sehgal | |
| 2013/0092622 A1 | 4/2013 | Kas et al. | |
| 2014/0116945 A1 | 5/2014 | Kas et al. | |
| 2015/0037055 A1 | 2/2015 | Kitagawa et al. | |
| 2015/0298070 A1 | 10/2015 | Koslov et al. | |
| 2015/0360157 A1 | 12/2015 | Hwang et al. | |

(56) References Cited

U.S. PATENT DOCUMENTS

| | | |
|---|---|---|
| 2016/0016124 A1 | 1/2016 | Zheng et al. |
| 2016/0136558 A1 | 5/2016 | Zheng et al. |
| 2016/0136584 A1 | 5/2016 | Hwang et al. |
| 2016/0166961 A1 | 6/2016 | Haberkamp et al. |
| 2016/0175748 A1 | 6/2016 | Park |
| 2016/0193555 A1 | 7/2016 | Park |
| 2017/0173509 A1 | 6/2017 | Giglia et al. |
| 2017/0173511 A1 | 6/2017 | Kas et al. |
| 2017/0360969 A1 | 12/2017 | Kozlov et al. |

FOREIGN PATENT DOCUMENTS

| | | | |
|---|---|---|---|
| CN | 1625429 | A | 6/2005 |
| CN | 1942616 | A | 4/2007 |
| CN | 101272840 | A | 9/2008 |
| CN | 101318090 | A | 12/2008 |
| CN | 102227247 | A | 10/2011 |
| CN | 102917777 | A | 2/2013 |
| DE | 19545701 | C1 | 5/1997 |
| EP | 0168783 | A1 | 1/1986 |
| EP | 0257635 | A2 | 3/1988 |
| EP | 0320033 | A1 | 6/1989 |
| EP | 0497594 | A1 | 8/1992 |
| EP | 0781600 | A2 | 7/1997 |
| EP | 1673493 | A1 | 6/2006 |
| EP | 1743975 | A1 | 1/2007 |
| EP | 1745808 | A1 | 1/2007 |
| EP | 1829603 | A1 | 9/2007 |
| EP | 1878482 | A1 | 1/2008 |
| EP | 2174703 | A1 | 4/2010 |
| EP | 2222385 | B1 | 9/2010 |
| EP | 2599908 | A1 | 6/2013 |
| GB | 1519070 | A | 7/1978 |
| JP | H2161954 | A | 6/1990 |
| JP | 200061277 | A | 2/2000 |
| JP | 2000325764 | A | 11/2000 |
| JP | 2004351645 | A | 12/2004 |
| JP | 2005515880 | A | 6/2005 |
| JP | 2005270965 | A | 10/2005 |
| JP | 2005536347 | A | 12/2005 |
| JP | 200682006 | A | 3/2006 |
| JP | 2006326579 | A | 12/2006 |
| JP | 2006341233 | A | 12/2006 |
| JP | 2007075739 | A | 3/2007 |
| JP | 2007105724 | A | 4/2007 |
| JP | 2007213876 | A | 8/2007 |
| JP | 2007301436 | A | 11/2007 |
| JP | 2007332342 | A | 12/2007 |
| JP | 200849239 | A | 3/2008 |
| JP | 2008162098 | A | 7/2008 |
| JP | 200950851 | A | 3/2009 |
| JP | 2009509754 | A | 3/2009 |
| JP | 2009148746 | A | 7/2009 |
| JP | 2009148748 | A | 7/2009 |
| JP | 2009183879 | A | 8/2009 |
| JP | 4351645 | B2 | 10/2009 |
| JP | 2009233550 | A | 10/2009 |
| JP | 201094962 | A | 4/2010 |
| JP | 2011/529778 | A | 12/2011 |
| JP | 2012520761 | A | 9/2012 |
| JP | 2012523320 | A | 10/2012 |
| JP | 2014208342 | A | 11/2014 |
| KR | 1020050077304 | A | 1/2004 |
| KR | 20060079211 | A | 7/2006 |
| KR | 100871440 | B1 | 12/2008 |
| KR | 20100037055 | A | 4/2010 |
| WO | WO-97/20622 | A1 | 6/1997 |
| WO | WO-1999/016810 | A1 | 4/1999 |
| WO | WO-200045933 | A1 | 8/2000 |
| WO | WO-2000/056804 | A1 | 9/2000 |
| WO | WO-2000/058388 | A1 | 10/2000 |
| WO | WO-200101047 | A1 | 1/2001 |
| WO | WO-01/14047 | A1 | 3/2001 |
| WO | WO-03/016601 | A1 | 2/2003 |
| WO | WO-2003/037959 | A1 | 5/2003 |
| WO | WO-03/064013 | A1 | 8/2003 |
| WO | WO-2003/080905 | A1 | 10/2003 |
| WO | WO-2004/018079 | A2 | 3/2004 |
| WO | WO-2005/024101 | A1 | 3/2005 |
| WO | WO-2005/073441 | A1 | 8/2005 |
| WO | WO-2006/016800 | A1 | 2/2006 |
| WO | WO-2006/068100 | A1 | 6/2006 |
| WO | WO-2006/131061 | A1 | 12/2006 |
| WO | WO-2006/131081 | A1 | 12/2006 |
| WO | WO-2007/001405 | A2 | 1/2007 |
| WO | WO-2007/041311 | A2 | 4/2007 |
| WO | WO-2007/054039 | A1 | 5/2007 |
| WO | WO-2007/054040 | A2 | 5/2007 |
| WO | WO-2007/054050 | A1 | 5/2007 |
| WO | WO-2007/098889 | A1 | 9/2007 |
| WO | WO-2007/111477 | A1 | 10/2007 |
| WO | WO-2007/137530 | A2 | 12/2007 |
| WO | WO-2007/144189 | A2 | 12/2007 |
| WO | WO-2008/034190 | A1 | 3/2008 |
| WO | WO-2008/073507 | A2 | 6/2008 |
| WO | WO-2008/106803 | A1 | 9/2008 |
| WO | WO-2008/106903 | A2 | 9/2008 |
| WO | WO-2008/109117 | A1 | 9/2008 |
| WO | WO-2008/142023 | A2 | 11/2008 |
| WO | WO-2009/010020 | A2 | 1/2009 |
| WO | WO-2009/017086 | A1 | 2/2009 |
| WO | WO-2009/032040 | A1 | 3/2009 |
| WO | WO-2009/063067 | A2 | 5/2009 |
| WO | WO-2009/064757 | A1 | 5/2009 |
| WO | WO-2009/064767 | A2 | 5/2009 |
| WO | WO-2009/071909 | A1 | 6/2009 |
| WO | WO-2010/042647 | A2 | 4/2010 |
| WO | WO-2010/042706 | A1 | 4/2010 |
| WO | WO-2010/049535 | A1 | 5/2010 |
| WO | WO-2010/069296 | A1 | 6/2010 |
| WO | WO-2010/107503 | A1 | 9/2010 |
| WO | WO-2010/120668 | A1 | 10/2010 |
| WO | WO-2011/019686 | A1 | 2/2011 |
| WO | WO-2011/151314 | A1 | 12/2011 |
| WO | WO-2012/021208 | A2 | 2/2012 |
| WO | WO-2012/021308 | A2 | 2/2012 |
| WO | WO-2012/135679 | A2 | 10/2012 |
| WO | WO-2013/013241 | A2 | 1/2013 |
| WO | WO-2014/093345 | A1 | 6/2014 |
| WO | WO-2014/159124 | A1 | 10/2014 |
| WO | WO-2015200239 | A1 | 12/2015 |

OTHER PUBLICATIONS

ASTM E1294-89 Withdrawal Notice, 2008, p. 1.
ASTM F316, 2003, pp. 1-7.
ASTM F838-05, "Standard Test Method for Determining Bacterial Retention of Membrane Filters Utilized for Liquid Filtration," 2005, 6 pages.
ASTM F838-83, "Standard Test Method for Determining Bacterial Retention of Membrane Filters Utilized for Liquid Filtration," 2005, 8 pages.
ASTM International, ASTM E1294-89 (1999) Withdraw Notice, Withdrawn Standard, Standard Test Method for Pore Size Characteristics of Membrane Filters Using Automated Liquid Porosimeter (Withdrawn 2008), p. 1.
ASTM International, Designation: D 1777-64, Reapproved 1975, "Standard Method for Thickness of Textile Materials," p. 477-478.
ASTM International, Designation: D1777, Reapproved 2011, "Standard Test Method for Thickness of Textile Materials," 5 pages.
ASTM International, Designation: D1777,"Standard Test Method for Thickness of Textile Materials,"(Reapproved 2015), Sep. 2015, 5 pages.
ASTM International, Designation: F316-03 (Reapproved 2011), Standard Test Methods for Pore Size Characteristics of Membrane Filters by Bubble Point and Mean Flow Pore Test, 2011, 7 pages.
ASTM International, Designation: F838-15, Standard Test Method for Determining Bacterial Retention of Membrane Filters Utilized for Liquid Filtration, 2015, 6 pages.
ATCC 19146 Product Data Sheet, "Brevundimonas diminuta," pp. 1-2.

(56) References Cited

OTHER PUBLICATIONS

Aussawasathien et al., "Separation of Micron to Sub-Micron Particles from Water: Electrospun Nylon-6 Nanofibrous Membranes as Pre-Filters," J Membrane Sci, 315: 11-19 (2008).
Barhate et al., "Nanofibrous filtering media: Filtration problems and solutions from tiny materials," J Membrane Sci, 296: 1-8 (2007).
Barhate et al., "Preparation and characterization of nanofibrous filtering media," J Membrane Sci, 283: 209-218 (2006).
Bhanushali et al., "Advances in Solvent-Resistant Nanofiltration Membranes: Experimental Observations and Applications," Ann Ny Acad Sci, vol. 984, Mar. 2003, pp. 159-177.
Bjorge et al., "Performance Assessment of Electrospun Nanofibers for Filter Applications," Desalination, 249 (3): 942-948 (Dec. 2009).
Blackwell, "Mycoplasma—Recent Developments in Detecting and in Preventing Bioreactor Contamination," 2005, IPSE Annual Meeting, Scottsdale, Arizona, Nov. 6-10, 2005, Slides 1-38, 38 pages.
Blanchard, "Quantifying Sterilizing Membrane Retention Performance," BioProcess International, 5(5): 44-51 (May 2007).
Blond et al., "Strong, Tough, Electrospun Polymer-Nanotube Composite Membranes with Extremely Low Density," Adv Funct Mater, 18: 2618-2624 (2008).
Chinese communciation, with English translation, dated Feb. 29, 2016 in co-pending Chinese patent application No. 201380070873.3.
Database WPI, "Week 200935," Thomson Scientific London, GB, 2009-F08014; XP002726900, 2 pages.
Deitzel et al., "The effect of processing variables on the morphology of electrospun nanofibers and textiles," Polymer, 42: 261-272 (2001).
Dimmock et al., Appendixes: Survey of Virus Properties, Vriuses with ssDNA genomes (class 2), Introduction to Modern Virology, Blackwell Publishing Limited, p. 450, 5 pages, 2007.
Doshi et al., "Electrospinning Process and Applications of Electrospun Fibers," J Electrostat, 35: 151-160 (1995).
Duan et al., "Preparing Graphitic Nanoribbons from Ultrathin Electrospun Poly(methyl methacrylate) Nanofibers by Electron Beam Irradiation," 2008 2nd IEEE International Nanoelectronics Conference (INEC 2008), 33-38.
Ebert et al., "Solvent Resistant Nanofiltration Membranes in Edible Oil Processing," Membrane Technology, vol. 107, 1999, pp. 5-8.
English translation WO 2010/069296 A1 (Jun. 2010).
English translation of Japanese communication, dated Apr. 11, 2016 in co-pending Japanese patent application No. 2014-502850.
European communication dated Jul. 20, 2016 in co-pending European patent application No. 13863417.5.
Extended European Search Report received for EP patent Application No. 07114167.5, dated Nov. 6, 2007, 7 pages.
Extended European Search Report received for EP Patent Application No. 10181774.0, dated Nov. 25, 2010, 5 pages.
Extended European Search Report received for EP patent Application No. 17195327, dated Aug. 16, 2018, 10 pages.
Final Rejection dated Apr. 30, 2014 in co-pending U.S. Appl. No. 13/436,043.
Final Rejection dated Aug. 7, 2014 in co-pending U.S. Appl. No. 13/257,501.
Final rejection dated Sep. 1, 2015 in co-pending U.S. Appl. No. 13/194,227.
Galka et al., "Trends in biopharmaceutical filtration and clarification," Filtr Separat, 44(3): Apr. 18-21, 2007.
Gibson et al., "Transport properties of porous membranes based on electrospun nanofibers," Colloid Surface A, 187-188: 469-481 (2001).
Gopal et al., "Electrospun Nanofibrous Polysulfone Membranes as Pre-Filters: Particulate Removal," J Membrane Sci, 289: 210-219 (2007).
Granath et al., "Molecular Weight Distribution Analysis by Gel Chromatography on Sephadex," J Chromatogr A, vol. 28, 1967, pp. 69-81.
Guo et al., "Cellulose Membrane used as Stationary Phase of Membrane Affinity Chromatography," Chinese Chem Lett, vol. 5, No. 10, 1994, pp. 869-872.
Hazel, "Ensuring Safety pf Biopharmaceuticals:Virus and Prion Safety Considerations," Filtration and Purification in the Biopharmaceutical Industry, 543-577 (2008).
Hou et al., "Poly (p-xylylene) Nanotubes by Coating and Removal of Ultrathin Polymer Template Fibers," Macromolecules, 35: 2429-2431 (2002).
Huang et al., "Electrospun polymer nanofibres with small diameters," Nanotechnology, 17: 1558-1563 (2006).
International Preliminary Report on Patentability dated Jan. 30, 2014 in corresponding PCT application No. PCT/US2012/047865.
International Preliminary Report on Patentability dated Oct. 10, 2013 in co-pending PCT application No. PCT/US2012/031549.
International Preliminary Report on Patentability dated Feb. 21, 2013 in co-pending PCT application No. PCT/US2011/045905.
International Preliminary Report on Patentability dated Jun. 25, 2015 in co-pending PCT application No. PCT/US2013/074132.
International Preliminary Report on Patentability dated Sep. 29, 2011 in co-pending PCT application No. PCT/US2010/000826.
International Preliminary Report on Patentability received for PCT Application No. PCT/US2010/000826 dated Sep. 26, 2011, 9 pages.
International Preliminary Report on Patentability received for PCT Patent Application No. PCT/US012/031549, dated Oct. 10, 2013, 10 pages.
International Preliminary Report on Patentability received for PCT Patent Application No. PCT/US2011/045805, dated Feb. 21, 2013, 7 pages.
International Preliminary Report on Patentability received for PCT Patent Application No. PCT/US2011/045905, dated Feb. 21, 2013, 7 pages.
International Search Report and Written Opinion dated Nov. 28, 2012 in co-pending PCT application No. PCT/US2012/031549.
International Search Report and Written Opinion dated Feb. 26, 2013 in co-pending PCT application No. PCT/US2012/047865.
International Search Report and Written Opinion dated Mar. 19, 2012 in co-pending PCT application No. PCT/US2011/045905.
International Search Report and Written Opinion dated Jun. 7, 2016 in co-pending PCT application No. PCT/US2016/018146.
International Search Report and Written Opinion dated Aug. 16, 2010 in co-pending PCT application No. PCT/US2010/000826.
International Search Report and Written Opinion dated Sep. 15, 2015 in co-pending PCT application No. PCT/US2015/037055.
International Search Report and Written Opinion received for PCT Application No. PCT/US2011/045905, dated Mar. 19, 2012, 13 pages.
International Search Report and Written Opinion received for PCT Application No. PCT/US2012/031549, dated Nov. 28, 2012, 15 pages.
International Search Report and Written Opinion received for PCT Application No. PCT/US2012/047665, dated Feb. 25, 2013, 18 pages.
International Search Report and Written Opinion Received for PCT Application No. PCT/US2016/018146, dated Jun. 7, 2016, 11 pages.
International Search Report and Written Opinion received for PCT Patent Application No. PCT/US2012/047865, dated Feb. 26, 2013, 18 pages.
International Search Report dated Mar. 21, 2014 in co-pending PCT application No. PCT/US2013/074132.
International Search Report received for PCT Application No. PCT/US2010/000826 dated Aug. 16, 2010, 5 pages.
Japanese communication, with English translation, dated Jun. 7, 2016 in co-pending Japanese patent application No. 2015-545930.
Japanese communication, with English translation, dated Mar. 18, 2014 in co-pending Japanese patent application No. 2013-524096.
Japanese communication, with English translation, dated Apr. 7, 2015 in co-pending Japanese patent application No. 2014-521858.
Kim et al., "Characterization and Properties of P (VdF-HFP)-Based Fibrous Polymer Electrolyte Membrane Prepared by Electrospinning," J Electrochem Soc, 152(2): A295-A300 (2005).

(56) References Cited

OTHER PUBLICATIONS

Korean communication, with English translation, dated Mar. 28, 2016 in co-pending Korean patent application No. 10-2013-7031748.

Lev et al., "Water Filtration by Nanotextiles," Conference Report from Nanocon, 6 pages (Oct. 2010).

Levit et al., "Supercritical CO2-assisted electrospinning," J Supercrit Fluid, 31: 329-333 (2004).

Li et al., "Collecting Electrospun Nanofibers with Patterned Electrodes," Nano Letters, 5(5): 913-916 (2005).

Lin et al., "Preparation of Poly(ether sulfone) Nanofibers by Gas-Jet/Electrospinning," J Appl Polym Sci, 107: 909-917 (2008).

Lyons et al., "Melt Electrospinning of Polymers: A Review," Polymer News, 30(6): 1-9 (2005).

Ma et al., "Electrospun cellulose nanofiber as affinity membrane," J Membrane Sci, 265: 115-123 (2005).

Ma et al., "Surface modified nonwoven polysulphone (PSU) fiber mesh by electrospinning: A novel affinity membrane," J Membrane Sci, 272: 179-187 (2006).

Ma et al., "Ultra Fine Cellulose Nanofibers: New Nano-Scale Materials for Water Purification," J Mater Chem, 21:7507-7510 (2011).

Meltzer et al., "Filtration and Purification in the Biopharmaceuticals Industry: Ensuring Safety of Biopharmaceuticals Virus and Prion Safety Considerations," 2nd edition, Informa Healthcare USA, Inc., Chapter 20, 2006, pp. 543-577.

Meltzer, T.H., "In Filtration in the Pharmaceutical Industry," Marcel Dekker, New York, 1987, p. 103.

Na et al., "Effects of Hot-Press on Electrospun Poly(vinylidene fluoride) Membranes," Polym Eng Sci, 48: 934-940 (2008).

Office Action dated Oct. 23, 2013 in co-pending U.S. Appl. No. 13/436,043.

Office Action dated Dec. 13, 2013 in co-pending U.S. Appl. No. 13/257,501.

Office Action dated Mar. 3, 2015 in co-pending U.S. Appl. No. 13/194,227.

Office Action dated Mar. 24, 2015 in co-pending U.S. Appl. No. 13/436,043.

Office Action dated Apr. 12, 2016 in co-pending U.S. Appl. No. 14/118,490.

Office Action dated Sep. 30, 2015 in co-pending U.S. Appl. No. 13/257,501.

Office Action—Restriction—dated Jul. 31, 2013 in co-pending U.S. Appl. No. 13/194,227.

Raghavan et al., "Novel electrospupn poly(vinylidene fluoride-co-hexafluoropropylene)-in situa SiO2 composite membrane-based polymer electrolyte for lithium batteries," J Power Sources, 184: 437-443 (2008).

Roche et al., "Methods Used to Validate Microporous Membranes for the Removal of Mycoplasma," BioPharm, 5(3): 22-23 (Apr. 1992).

Rutledge et al., "Formation of fibers by electrospinning," Adv Drug Deliver Rev, 59: 1384-1391 (2007).

Sang et al., "Filtration by a novel nanofiber membrane and alumina adsorption to remove cooper(II) from groundwater," J Hazard Mater, 153: 860-866 (2008).

Sang et al., "Heavy metal-contaminated groundwater treatment by a novel nanofiber membrane," Desalination, 223: 349-360 (2008).

Segers et al., "Classification' of Pseudomonas diminuta Leifson and Hugh 1954 and Pseudomonas vesicularis Büsing, Döll, and Freytag 1953 in Brevundimonas gen. nov. as Brevundimonas diminuta comb. nov. and Brevundimonas vesicularis comb. nov., Respectively," Int J Syst Bacteriol, 44(3): 499-510 (Jul. 1994).

Sill et al., "Electrospinning: Applications in drug delivery and tissue engineering," Biomaterials, 29: 1989-2006 (2008).

Smit et al., "Continuous yarns from electrospun fibers," Polymer, 46: 2419-2423 (2005).

Tan et al., "Systematic parameter study for ultra-fine fiber fabrication via electrospinning process," Polymer, 46: 6128-6134 (2005).

Teo et al., "A review on electrospinning design and nanofibre assemblies," Nanotechnology, 17: R89-R106 (2006).

Wang et al., "Electrospun nanofibrous membranes for high flux microfiltration," J Membrane Sci, 392-393: 167-174 (2012).

Yarin et al., "Upward needleless electrospinning of multiple nanofibers," Polymer, 45: 2977-2980 (2004).

Yoon et al., "High flux ultrafiltration membranes based on electrospun nanofibrous PAN scaffolds and chitosan coating," Polymer, 47: 2434-2441 (2006).

Yoshimatsu et al., "Selective molecular adsorption using electrospun nanofiber affinity membranes," Biosens Bioelectron, 23: 1208-1215 (2008).

Yun et al., "Nanoparticle filtration by electrospun polymer fibers," Chem Eng Sci, 62: 4751-4759 (2007).

Zeman et al., "Steric Rejection of Polymeric Solutes by Membranes with Uniform Pore Size Distribution," Separ Sci Technol, vol. 16 (3): 275-290 (Apr. 1981).

Zhao et al., "Preparation and Properties of Electrospun Poly (Vinylidene Fluoride) Membranes," J Appl Polym Sci, 97: 466-474 (2005).

Zwijnenberg et al., "Acetone-Stable Nanofiltration Membranes in Deacidifying Vegetable Oil," J Am Oil Chem Soc, vol. 76 (1): 83-87 (1999).

* cited by examiner

REMOVAL OF MICROORGANISMS FROM FLUID SAMPLES USING NANOFIBER FILTRATION MEDIA

CROSS REFERENCED TO RELATED APPLICATIONS

This application is a Continuation of application Ser. No. 15/691,286, which is a Continuation of application Ser. No. 13/257,501, which is the National Stage of International Application No. PCT/US10/00826 filed on Mar. 19, 2010, which claims the benefit of U.S. Provisional Application 61/210,468 filed on Mar. 19, 2009. The entire contents of these applications are incorporated herein by reference in their entirety.

FILED OF THE INVENTION

The present invention relates generally to filtration media. In certain embodiments, the invention provides a porous electrospun nanofiber liquid filtration mat, and methods of using the same in the retention of microorganism from a filtered liquid.

BACKGROUND OF THE INVENTION

Filters used in liquid filtration can be generally categorized as either fibrous nonwoven media filters or porous film membrane filters.

Fibrous nonwoven liquid filtration media include, but are not limited to, nonwoven media formed from spunbonded, melt blown or spunlaced continuous fibers; hydroentangled nonwoven media formed from carded staple fiber and the like or some combination of these types. Typically, fibrous nonwoven filter media filters used in liquid filtration have pore sizes generally greater than about 1 micron (μm).

Porous film membrane liquid filtration media is used either unsupported or used in conjunction with a porous substrate or support. Porous filtration membranes have pore sizes smaller than the fibrous nonwoven media, and typically have pore sizes less than about 1 μm. Porous film liquid filtration membranes can be used in (a) microfiltration, wherein particulates filtered from a liquid are typically in the range of about 0.1 μm to about 10 μm; (b) ultrafiltration, wherein particulates filtered from a liquid, are typically in the range of about 5 nm to about 0.1 μm; and (c) reverse osmosis, wherein particulate matter filtered from a liquid, are typically in the range of about 1 Å to about 1 nm.

Fibrous nonwoven media and porous film membranes are each suitable for use in microfiltration. Microfiltration is widely accepted in industry as a reliable, easily scalable, and benign method to remove microorganisms, such as bacteria, from a fluid stream, and is an essential part of pharmaceutical and biopharmaceutical manufacturing. It is especially important in the biopharmaceutical industry, where microfiltration is used at multiple locations during biopharmaceutical processing.

However, in order to achieve particle retentions equivalent to pore sizes of less than about 1 μm using microfiltration with a fibrous nonwoven media, the number of layers of fibrous material the filter needs to be increased in order to increase the depth of the nonwoven media. Increasing the number of fibrous layers in the nonwoven media produces both desirable and undesirably results. Increasing the number of fibrous layers produces desirable results by increased tortuosity of a defect path through which a contaminant particle must pass to escape capture by the filter media as well as increasing the contaminant-holding capacity of the filter media. However, increasing the number of fibrous layers in nonwoven media undesirably increases the pressure drop or differential pressure across the media when in use, which translates to increased energy for the filter user and a shorter filter lifespan.

Porous membrane filters used in microfiltration, unlike fibrous nonwoven media, offer a combination of good particle retention, pressure drop and flux, but also tend to be cost-prohibitive, and typically do not provide good contaminant-holding capacity over the entire range of pressure drop, therefore limiting the life of filters using porous membranes.

The two most desired features of liquid microfiltration membrane are high permeability and reliable retention. Naturally, there is a trade-off between these two parameters, and for the same type of membrane, greater retention has historically been achieved by sacrificing permeability of the membrane. The inherent limitations of the conventional processes for making membranes prevents membranes from exceeding a certain threshold in porosity, and thus limits the magnitude of permeability that can be achieved at a given pore size.

A quantitative measure of microorganism retention by a filtration membrane is customarily expressed as a Log Reduction Value, or LRV. LRV is a logarithm of the ratio of particle concentration in the challenge solution to that in the filter effluent:

$$LRV = Log\{[CFU]_{challenge}/[CFU]_{effluent}\}$$

In the case when the filter retains all microorganisms under the conditions of the test, it is customarily to report the LRV as greater than the value obtained when a single microorganism passes the filter. For example, at the challenge particle concentration of $4.77*10^7$ CFU/cm$^2$, the maximum measurable LRV is 8.22. When no particles pass the filter, the LRV is reported as greater than 8.22.

Pore size rating of a membrane is an indicator that the membrane has successfully passed a relevant, standardized bacterial challenge test. The most common pore size rating is 0.22 μm, which is assigned to membranes that pass a Standard Test Method for Determining Bacterial Retention Of Membrane Filters Utilized For Liquid Filtration (ASTM F838-83 test), can be validated to produce sterile effluent after being challenged with $\geq 10^7$ CFU/cm$^2$ *Brevundimonas diminuta*.

*Brevundimonas diminuta* (ATTC #19146), formerly known as *Pseudomonas diminuta*, is an aerobic gram-negative bacteria (bacilli). Because of its small size, *B. diminuta* is a standard microbial organism for validation of membrane filters and the like for sterilization. However, while *B. diminuta* is representative of most pathogenic bacteria, *B. diminuta* has proved to be a poor model for a class of microorganisms called *Mycoplasma*. While representative of most pathogenic bacteria, *B. diminuta* has proved to be a poor model for a class of microorganisms called *Mycoplasma*.

*Mycoplasma* is a microorganism that can infect cell cultures and can have a substantially deleterious effect to biopharmaceutical manufacturing. The contamination of eukaryotic cell cultures and the like with *Mycoplasma* is also a common problem, leading to unreliable experimental results and possibly unsafe biological products. This represents a serious problem for manufacturers involved in the development and fabrication of biological and pharmaceutical products. The highly nutritive environment of the media used in cell culture can lead to the propagation of *Mycoplasmas*, resulting in diminished cell growth as well as the loss of cultures. In contrast to contamination with types of bacteria which can be detected in a short period after infection on the basis of visible effects such as cytopathicity, pH change, abnormal growth, the media appearing turbid, contamination caused by *Mycoplasma* may go undetected without noticeable symptoms (Razin, S. 1997. Comparative genomics of *Mycoplasmas*. Wien Klin Wochenschr 109: 551-6. Jung H, Wang S Y, Yang I W, Hsueh W, Yang W J, Wang T H, Wang: H S. (2003) Detection and treatment of *Mycoplasma* contamination in cultured cells, Chang Gung Med J. 26: 250-8 Wisher M. (2002) Biosafety and product release testing issues relevant to replication-competent oncolytic viruses, Review, Cancer Gene Ther. 9: 1056-61).

A membrane pore size rating of 0.1 µm indicates that a membrane has been validated to remove *Mycoplasma*. (See, Roche, K. L.: Levy, R. V., Methods to Validate Microporous Membranes for the Removal of *Mycoplasma*, BioPharm 1992, 5, (3), 22-33)

For example, membranes having a pore size rating of 0.1 µm can be used to filter media, nutrient and cell culture fluid delivered to cells living and growing inside of a bioreactor. Membranes currently exist that have a specific Log Reduction Value (LRV) for *A. Laidawii*, a test microorganism for *Mycoplasma*. While it is customarily accepted that LRV>8 is sufficient to claim "full" retention of *Mycoplasma*, filters having a lower LRV are often used instead in liquid filtration because of greater permeability and higher throughput.

WO/2009/032040, assigned to Millipore Corporation and titled, SERUM-FREE GROWTH MEDIUM FOR *ACHOLEPLASMA LAIDLAWII* AND METHODS FOR RETENTION TESTING STERILIZING GRADE FILTERS, fully incorporated by reference herein in its entirety, teaches the full retention of *Mycoplasma* by a filtration medium can be validated to produce sterile effluent after being challenged with ≥1 $10^9$×cfu/mL *Acholeplasma laidlawii* (*A. laidlawii*; ATCC 23206).

For example, two membranes having a pore size rating of 0.1 µm, Durapore® VV and Express SHR, each available from Millipore Corporation, Billeric Mass., USA, have *Mycoplasma* LRVs of 4 and 6, respectively. While Durapore® MV, also available from Millipore Corporation, claims full *Mycoplasma* retention (LRV>8), it has a lower permeability and capacity in media filtration compared to Durapore® VV and Express SHR.

Synthetic polymers have been formed into webs of very small diameter fibers, i.e., on the order of a few micrometers or less than 1 µm, using various processes including melt blowing, electrostatic spinning and electroblowing. Such webs have been shown to be useful as liquid barrier materials and filters. Often they are combined with stronger sheets to form composites, wherein the stronger sheets provide the strength to meet the needs of the final filter product.

U.S. Patent Publication Number 2004/0038014 is issued to Schaefer et al. teaches a nonwoven filtration mat comprising one or more layers of a thick collection of fine polymeric microfibers and nanofibers formed by electrostatic spinning for filtering contaminants. The electrostatic spinning process utilizes an electro spinning apparatus including a reservoir in which the fine fiber forming polymer solution is contained, a pump and an emitter device which obtains polymer solution from the reservoir. In the electrostatic field, a droplet of the polymer solution is accelerated by the electrostatic field toward a collecting media substrate located on a grid. A high voltage electrostatic potential maintained between the emitter and grid, with the collection substrate positioned there between, by means of a suitable electrostatic voltage source.

The "electroblowing" process is disclosed in World Patent Publication No. WO 03/080905, incorporated herein by reference in its entirety. A stream of polymeric solution comprising a polymer and a solvent is fed from a storage tank to a series of spinning nozzles within a spinneret, to which a high voltage is applied and through which the polymeric solution is discharged. Meanwhile, compressed air that is optionally heated is issued from air nozzles disposed in the sides of, or at the periphery of the spinning nozzle. The air is directed generally downward as a blowing gas stream which envelopes and forwards the newly issued polymeric solution and aids in the formation of the fibrous web, which is collected on a grounded porous collection belt above a vacuum chamber. The electroblowing process permits formation of commercial sizes and quantities of nanowebs at basis weights in excess of about 1 gsm, even as high as about 40 gsm or greater, in a relatively short time period.

U.S. Patent Publication Number 2007/0075015 issued to Bates et al. teaches a liquid filtration media including at least one layer of nanofibers having average diameters less than 1,000 nanometers optionally disposed on scrim layer for filtering particulate matter in a liquid. The filtration media have flow rates of at least 0.055 L/min/cm$^2$ at relatively high levels of solidity. The media apparently has non-diminishing flow rates as differential pressures increase between 2 psi (14 kPa) and 15 psi (100 kPa).

U.S. Patent Publication Number 2007/0018361 issued to Xu teaches fabricating nanofibers by reactive electrospinning, wherein the electrospinning process is coupled with an in-line reactor where chemical or photochemical reactions take place. The processes taught in Xu use electrospinning to allow for the production of nanofibers from crosslinked polymers and other materials.

U.S. Patent Publication Number 2009/0026137 issued to issued to Chen teaches fabricating liquid filter with a composite medium that has a nanoweb adjacent to and optionally bonded to a microporous membrane. The membrane is characterized by an LRV value of 3.7 at a rated particle size, and the nanoweb has a fractional filtration efficiency of greater than 0.1 at the rated particle size of the membrane. The nanoweb also has a thickness efficiency ratio of greater than 0.0002 at that efficiency. The nanoweb acts to provide depth filtration to the membrane.

It would be desirable to have a reliable electrospun nanofiber liquid filtration medium having a microorganism LRV greater than about 8, suitable for full retention of microorganisms such as bacteria, *Mycoplasma* in particular, and/or a *B. Diminuta* LRV greater than about 9, suitable for full retention of *B. Diminuta*, when removed from a liquid passing through the filtration medium, while simultaneously achieving high permeability and high throughput.

Additionally, the porous electrospun nanofiber filtration medium would be readily scalable, adaptable to processing volumes of sample fluids ranging from milliliters to thousands of liters, and capable of use with a variety of filtration processes and devices. The invention is directed to these, as well as other objectives and embodiments.

SUMMARY OF THE INVENTION

The present invention is directed to a method of removing microorganisms from a liquid by passing the liquid through a porous electrospun nanofiber liquid filtration medium. The electrospun nanofiber liquid filtration medium can be used with or without being disposed on a porous support or substrate. The electrospun nanofiber liquid filtration medium can be formed into a variety of shapes, sizes, thicknesses and densities, such as a porous, polymeric nanofiber mat.

In another embodiment, the present invention is directed towards porous, electrospun nanofiber liquid filtration medium having a *B. Diminuta* LRV greater than about 9, and the nanofiber(s) has an average fiber diameter ranging from about 10 nm to about 1000 nm.

In another embodiment, the present invention is directed towards a porous electrospun nanofiber liquid filtration medium having a *B. Diminuta* LRV greater than about 9, and the filtration medium has a porosity ranging from about 80% to about 95%.

In another embodiment, the present invention is directed towards a porous electrospun nanofiber liquid filtration medium having a *Mycoplasma* LRV greater than about 4, and a liquid permeability at 10 psi differential pressure greater than about 3,000 LMH. (Liters Per Square Meter Per Hour).

In another embodiment, the present invention is directed towards a porous electrospun nanofiber liquid filtration medium having a *Mycoplasma* LRV greater than about 8, and a liquid permeability at 10 psi differential pressure greater than about 3,000 LMH.

In another embodiment, the present invention is directed towards a porous electrospun nanofiber liquid filtration medium having a *B. Diminuta LRV greater than about* 9, and formed as a fibrous porous mat having a thickness ranging from about 1 μm to about 500 μm.

In another embodiment, the present invention is directed towards a porous electrospun nanofiber liquid filtration medium having a *B. Diminuta* LRV greater than about 9, and a liquid permeability at 10 psi differential pressure greater than about 10,000 LMH.

In another embodiment, the present invention is directed towards a porous electrospun nanofiber liquid filtration medium having a *Mycoplasma* LRV greater than about 8, and the nanofiber(s) has an average fiber diameter ranging from about 10 nm to about 1,000 nm.

In another embodiment, the present invention is directed towards a porous electrospun nanofiber liquid filtration medium having a *Mycoplasma* LRV greater than about 8, and a liquid permeability at 10 psi differential pressure greater than about 3,000 LMH.

In another embodiment, the present invention directed towards a porous electrospun nanofiber liquid filtration medium having a *Mycoplasma* LRV greater than about 8, and the filtration medium has a porosity ranging from about 80% to about 95%.

In another embodiment, the present invention is directed towards a porous electrospun nanofiber liquid filtration medium having a *Mycoplasma* LRV greater than about 8, and formed as a fibrous porous mat having a thickness ranging from about 1 μm to about 500 μm.

In another embodiment, the present invention is directed towards a porous electrospun nanofiber liquid filtration medium having a *Mycoplasma* LRV greater than about 8, and a liquid permeability at 10 psi differential pressure greater than about 10,000 LMH.

In another embodiment, the present invention is directed to a process for forming a porous filtration medium from one or more electrospun polymeric nanofibers from a polymer solution by using an electrospinning apparatus, and subjecting the solution to an electric potential greater than about 10 kV, and collecting electrospun polymer fiber(s) as a non-woven mat.

In another embodiment, the present invention is directed to a composite porous filtration device comprising a filtration medium having a microorganism LRV greater than about 8, and including an electrospun polymeric nanofiber mat disposed on a porous support or porous substrate.

Additional features and advantages of the invention will be set forth the detailed description and claims, which follows. Many modifications and variations of this invention can be made without departing from its spirit, and scope, as will be apparent to those skilled in the art. It is to be understood that the foregoing general description and the following detailed description, the claims, as well as the appended drawings are exemplary and explanatory only, and are intended to provide an explanation of various embodiments of the present teachings. The specific embodiments described herein are offered by way of example only and are not meant to be limiting in any way.

BRIEF DESCRIPTION OF THE DRAWINGS

The accompanying drawings, which are incorporated in and constitute a part of this specification, illustrate the presently contemplated embodiments of the invention and, together with the description, serve to explain the principles of the invention.

FIG. 1 is a schematic of the process of electrospinning a nonfiber according to one embodiment of the invention. Polymer solution 10, rotating drum 20, moving collecting belt 30, ground electrode 35, high voltage source 40, polymer fibers produced by electric field 50, fiber mat 60 formed from polymer fibers.

FIG. 2 is a cross-sectional scanning electron micrograph of nylon fibers from an embodiment of the invention exemplified in Example 1.

FIG. 3 is a frontal scanning electron micrograph of nylon fibers from an embodiment of the invention exemplified in Example 1.

FIG. 4 is a scanning electron micrograph of nylon fibers from another embodiment of the invention as exemplified in Example 2.

FIG. 5 is a scanning electron micrograph of a symmetrical commercial membrane Durapore® MVPP from Comparative Example 1.

FIG. 6 is a scanning electron micrograph of a symmetrical commercial membrane Durapore® GVPP from Comparative Example 2.

DESCRIPTION OF THE EMBODIMENTS

All publications, patents end patent applications cited herein, whether supra or infra, are hereby incorporated by reference in their entirety to the same extent as if each individual publication, patent or patent application was specifically and individually indicated to be incorporated by reference.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about".

Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Before describing the present invention in further detail, a number of terms will be defined. Use of these terms does not limit the scope of the invention but only serve to facilitate the description of the invention.

As used herein, the singular forms "a," "an" and "the" include plural referents unless the context clearly dictates otherwise.

The term "nanofibers" refers to fibers having diameters varying from a few tens of nanometers up to several hundred nanometers, but generally less than one micrometer.

The terms "filter medium" or "filter media" refer to a material, or collection of material, through which a fluid carrying a microorganism contaminant passes, wherein microorganism is deposited in or on the material or collection of material.

The terms "flux" and "flow rate" are used interchangeably to refer to the rate at which a volume of fluid passes through a filtration medium of a given area.

The filtration medium of the present invention includes a porous electrospun nanofiber liquid filtration mat. The nanofibers have an average fiber diameter of about 10 nm to about 1000 nm. The filtration medium has a mean pore size ranging from about 0.1 µm to about 1 µm. The filtration medium has a porosity ranging from about 80% to about 95%. The filtration medium has a thickness ranging from about 1 µm to about 500 µm, preferably from about 50 µm and about 200 µm. The filtration medium has liquid permeability greater than about 300 LMH/psi.

Polymers suitable for use in the nanofibers of the invention include thermoplastic and thermosetting polymers. Suitable polymers include, but are not limited to, nylon, polyimide, aliphatic polyamide, aromatic polyamide, polysulfone, celluose, cellulose acetate, polyether sulfone, polyurethane, poly(urea urethane), polybenzimidazole, polyetherimide, polyacrylonitrile, poly(ethylene terephthalate), polypropylene, polyaniline, poly(ethylene oxide), poly(ethylene naphthalate), poly(butylene terephthalate), styrene butadiene rubber, polystyrene, poly(vinyl chloride), poly(vinyl alcohol), poly(vinylidene fluoride), poly(vinyl butylene), copolymers, derivative compounds and blends thereof, and combinations thereof.

The process for making the electrospun nanofiber mat of the filtration medium is disclosed in WO 2005/024101; WO 2006/131081; and WO 2008/106903, all assigned to Elmarco S.R.O., of Liberec, Czech Republic.

In one embodiment of the present invention, the filtration medium comprises a mat made from a single nanofiber, wherein the single nanofiber is made by a single pass of a moving collection apparatus positioned between the spinning drum and the collector through the process. It will be appreciated that the fibrous web can be formed by one or more spinning drums running simultaneously above the same moving collection apparatus.

In one embodiment of the invention, a fibrous mat is made by depositing nanofiber (s) from a nylon solution. The nanofiber mat has a basis weight of between about 5 g/m$^2$ and about 15 g/m$^2$, as measured on a dry basis, i.e., after the residual solvent has evaporated or been removed.

As depicted in FIG. 1, a moving collection apparatus 30 is preferably a moving collection belt positioned within the electrostatic field between the spinning beam 20 and the collector 35, wherein the porous mat made from a single nanofiber is collected.

In one embodiment of the invention, any of a variety of porous single or multilayered substrates or supports can be arranged on a moving collection belt to collect and combine with the electrospun nanofiber mat medium, forming a composite filtration device.

Examples of single or multilayered porous substrates or supports include, but are not limited to, spunbonded nonwovens, meltblown nonwovens, needle punched nonwovens, spunlaced nonwovens, wet laid nonwovens, resin-bonded nonwovens, woven fabrics, knit fabrics, paper, and combinations thereof.

In another embodiment of the invention the electrospun the nanofiber mat medium taught herein may be bonded a porous substrate or support. Bonding may be accomplished by known methods in the art, including but not limited to thermal calendaring between heated smooth nip rolls, ultrasonic bonding, and through gas bonding. Bonding increases the strength and the compression resistance of the medium so that the medium may withstand the forces associated with being handled, being formed into a useful filter, and being used in a filter, and depending on the bonding method used, adjusts physical properties such as thickness, density, and the size and shape of the pores.

For instance, thermal calendering can be used reduce the thickness and increase the density and reduce the porosity of the electrospun nanofiber mat medium, and reduce the size of the pores. This in turn decreases the flow rate through the medium at a given applied differential pressure. In general, ultrasonic bonding will bond to a smaller area of the electrospun nanofiber mat medium than thermal clendering, and therefore has a lesser effect on thickness, density and pore size. Though gas bonding generally has minimal effect on thickness, density and pore size, therefore this bonding method may be preferable in applications in which maintaining higher fluid flow rate is desired.

When thermal calendering is used, care must be taken not to over-bond the electrospun nanofiber material, such that the nanofibers melt and no longer retain their structure as individual fibers. In the extreme, over-bonding would result in the nanofibers melting completely such that a film would be formed. One or both of the nip rolls used is heated to a temperature of between about ambient temperature, e.g., about 25° C. and about 300° C. The nanofiber mat(s) and/or porous support or substrate, can be compressed between the nip rolls at a pressure ranging from about 0 lb/in to about 1000 lb/in (178 kg/cm). The nanofiber mat(s) can be compressed at a line speed of at least about 10 ft/min (3 m/min).

Calendering conditions, e.g., roll temperature, nip, pressure and line speed, can be adjusted to achieve the desired solidity. In general, application of higher temperature, pressure, and/or residence time under elevated temperature and/or pressure results in increased solidity.

Other mechanical steps, such as stretching, cooling, heating, sintering, annealing, reeling, unreeling, and the like, may optionally be included in the overall process of forming, shaping and making the electrospun nanofiber mat medium as desired.

For example, the electrospun nanofiber mat medium taught herein may be stretched in a single step or a plurality of steps as desired. Depending on the stretching method used to stretch the electrospun nanofiber mat medium, stretching can adjust the physical properties of the mat including thickness, density, and the size and shape of the pores formed in the mat. For example, if the electrospun nanofiber mat is stretched in a single direction (uniaxial stretching), the stretching may be accomplished by a single stretching step or a sequence of stretching steps until the desired final stretch ratio is attained.

Similarly, if the electrospun nanofiber mat medium is stretched in two directions (biaxial stretching), the stretching can be conducted by a single biaxial stretching step or a sequence of biaxial stretching steps until the desired final stretch ratios are attained. Biaxial stretching may also be accomplished by a sequence of one or more uniaxial stretching steps in one direction and one or more uniaxial stretching steps in another direction. Biaxial stretching steps where the electrospun nanofiber mat is stretched simultaneously in two directions and uniaxial stretching steps may be conducted in sequence in any order.

Methods for stretching the mat are not particularly limited, and use may be made of ordinary tentering, rolling, or inflation or a combination of two or more of these. The stretching may be conducted uniaxially, biaxially, etc. In the case of biaxial stretching, machine-direction stretching and transverse-direction stretching may be conducted either simultaneously or successively.

Various types of stretching apparatus are well known in art and may be used to accomplish stretching of the electrospun mat according to the present invention. Uniaxial stretching is usually accomplished by stretching between two rollers wherein the second or downstream roller rotates at a greater peripheral speed than the first or upstream roller. Uniaxial stretching can also be accomplished on a standard tentering machine.

Biaxial stretching may be accomplished by simultaneously stretching in two different directions on a tentering machine. More commonly, however, biaxial stretching is accomplished by first uniaxially stretching between two differentially rotating rollers as described above, followed by either uniaxially stretching in a different direction using a tenter machine or by biaxially stretching using a tenter machine. The most common type of biaxial stretching is where the two stretching directions are approximately at right angles to each other. In most cases where a continuous sheet is being stretched, one stretching direction is at least approximately parallel to the long axis of the sheet (machine direction) and the other stretching direction is at least approximately perpendicular to the machine direction and is in the plane of the sheet (transverse direction).

After the electrospun nanofiber mat has been stretched either uniaxially or biaxially, the stretched porous electrospun nanofiber mat can again be calendared. The stretched electrospun nanofiber mat can be forwarded to a pair of heated calendar rolls acting cooperatively so as to form a mat of reduced thickness compared to the mat exiting from the stretching apparatus. By regulating the pressure exerted by these calendar rolls along with the temperature, the pore size of the final electrospun nanofiber mat can be controlled as desired, thereby allowing for the adjustment of the average pore size.

The electrospun nanofiber mat may be heated by any of a wide variety of techniques prior to, during, and/or after stretching. Examples of these techniques include radiative heating such as that provided by electrically heated or gas fired infrared heaters, convective heating such as that provided by recirculating hot air, and conductive heating such as that provided by contact with heated rolls. The temperatures which are measured for temperature control purposes may vary according to the apparatus used and personal preference.

In general, the temperature or temperatures can be controlled such that the electrospun nanofiber mat is stretched about evenly so that the variations, if any, in thickness of the stretched mat are within acceptable limits and so that the amount of stretched microporous electrospun nanofiber mat outside of those limits is acceptably low. It will be apparent that the temperatures used for control purposes may or may not be close to those of the electrospun nanofiber mat itself since they depend upon the nature of the apparatus used, the locations of the temperature-measuring devices, and the identities of the substances or objects whose temperatures are being measured.

The porosity can be modified as a result of calendering. The range of porosity from about 5% to about 90% can be obtained.

While filtration medium is often used in single-layer configuration, it is sometimes advantageous to provide more than one layer of filtration medium adjacent to each other. Layering membrane filters to improve particle retention is commonly used in virus filtration and is practiced commercially its Millipore's product lines of Viresolve® NFP and Viresolve Pro®. Layering filtration media of the same or different composition is also used to improve filter throughput. Examples of such layered filters are Millipore's Express® SHC and SHRP product lines. Other considerations for choosing a multi-layered filtration product include economics and convenience of media and device manufacturing, ease of sterilization and validation. The fibrous filtration, media of the present invention can be used in single-layer or in a multi-layer configuration.

Test Methods

Basis Weight was determined by ASTM D-3776, which is hereby incorporated by reference and reported in $g/m^2$.

Porosity was calculated by dividing the basis weight of the sample in $g/m^2$ by the polymer density in $g/cm^3$, by the sample thickness in micrometers, multiplying by 100, and subtracting the resulting number from 100 porosity=100−[basis weight/(density·times·thickness)·times·100].

Fiber Diameter was determined as follows. Ten scanning electron microscope (SEM) images at 40,000·times. Magnification was taken of each nanofiber layer sample. The diameter of ten (10) clearly distinguishable nanofibers were measured from each SEM image and recorded. Defects were not included lumps of nanofibers, polymer drops, intersections of nanofibers). The average fiber diameter for each sample was calculated.

Thickness was determined by ASTM D1777-64, which is hereby incorporated by reference, and is reported in micrometers.

Mean flow bubble point was measured according to ASTM Designation E 1294-89, "Standard Test Method for Pore Size Characteristics of Membrane Filters Using Automated Liquid Porosimeter" by using automated bubble point method from ASTM Designation F 316 using a custom-built capillary flow porosimeter, in principle similar to a commercial apparatus from Porous Materials, Inc, (PMI), Ithaca, N.Y. Individual samples of 47 mm in diameter (9.6 cm² measurable area) were wetted with isopropyl alcohol. Each sample was placed in a holder, and a differential pressure of air was applied and the fluid removed from the sample. The differential pressure at which wet flow is equal to one-half the dry flow (flow without wetting solvent) is used to calculate the moan flow pore size using supplied software.

Flow Rate (also referred to as Flux) is the rate at which fluid passes through the sample of a given area and was measured by passing deionized water through filter medium samples having a diameter of 35 mm. The water was forced through the samples using hydraulic pressure (water head pressure) or pneumatic pressure (air pressure over water).

The effective pore size of an electrospun mat can be measured using conventional membrane techniques such as bubble point, liquid-liquid porometry, and challenge test with particles of certain size. It is known that the effective pore size of a fibrous mat generally increases with the fiber diameter and decreases with porosity.

Bubble point test provides a convenient way to measure effective pore size. It is calculated from the following equation:

$$P = \frac{2\gamma}{r}\cos\theta,$$

where P is the bubble point pressure, γ is the surface tension of the probe fluid, r is the pore radius, and θ is the liquid-solid contact angle.

*B. Diminuta* retention was measured in accordance with ASTM F883-83.

The following Examples of the present invention will demonstrate that an electrospun nanofiber mat can possess both high permeability and high bacteria retention at the same time.

Hereinafter the present invention will be described in more detail in the following examples. The invention will be further clarified by the following examples which are intended to be exemplary of the invention.

EXAMPLES

Example 1

An electrospinning process and apparatus for forming a nanofiber web as disclosed in WO 2006/131081 was used to produce the nanofiber layers and mats of the Examples below.

Nanofiber layers were made by electrospinning a solution of Nylon 6 polymer. Nylon 6 was supplied by BASF Corp., Florham Park, N.J., USA, under the trademark Ultramid B24. A solvent mixture of acetic and formic acid, weight ratio 2:1, was used to prepare solutions of Nylon, with concentrations ranging from 8 to 16%.

A 10 wt % solution of Nylon was electrospun at 82 kV and distance between solution and ground electrode 155 mm, for 45 minutes. By way of example only, samples were tested for *A. Laidiawii* retention using standard Millipore procedures described above. A representative sample is compared to the closest Durapore® membrane, MVPP, in Table I below.

The results are shown in Table I below.

TABLE I

| | Thickness (micron) | Permeability (LMH/psi) | Mean flow bubble point for IPA (psi) | Nominal pore size rating (micron) | Porosity (%) | *A. Laidlawii* LRV |
|---|---|---|---|---|---|---|
| Example 1: Electrospun Nylon 140 | 140 | 400 | 65 | N/A | 88 | >8.6 |
| Comparative Example 1: Millipore Durapore ® MVPP | 125 | 80 | 55 | 0.1 | 70 | >8.6 |

Membrane manufacturers assign nominal pore size ratings to commercial membrane filters, which are based on their retention characteristics.

While it is known that the pore size distribution of a random non-woven mat becomes narrower as thickness of the mat increases (See, Meltzer, T. H., In Filtration in the Pharmaceutical Industry, Marcel Dekker: New York, 1987; p 103) it has not been previously shown whether the pore size distribution of a non-woven mat can be sufficiently narrow to accomplish "full bacteria retention" (as discussed supra) at competitive permeability of at least 100 LMH/psi for *Mycoplasma*-retentive filters and 500 LMH/psi for *B. Diminuta*-retentive filters.

*Mycoplasma* retention was measured by challenging the membranes with 8.77*10⁷ colony forming units per square cm of membrane (CFU/cm²). The devices are challenged with 50 mL of diluted *A. laidlawii* and then flushed with 50 mL of *Mycoplasma* Buffer for a total of 100 mL. The full 100 mL was then filtered through a 022 μm sterilization membrane. Then, the procedure described in a published patent application WO 2009/032040 was followed.

Example 2

A series of Nylon 6 electrospun fibrous mats were prepared as described in Example 1. A 13 wt. % solution of Nylon was electrospun at 82 kV and distance between solution and ground electrode 155 mm, for 10 and 45 minutes. Fiber mats of 55 and 225 microns thick were produced for the two spin times, respectively. These samples were tested, by way of example only, for *B. Diminuta* retention. It should be noted that the *Mycoplasma*-retentive electrospun fibrous mats as taught herein are used for the full retention of *B. Diminuta*.

Example 3

Another series of Nylon 6 electrospun fibrous mats were prepared as described in Example 2. A 16 wt % solution of Nylon was electrospun at 82 kV and distance between solution and ground electrode 155 mm, for 15 minutes. These samples were tested, by way of example only, for *B. Diminuta* retention.

The results are shown in Table II below.

TABLE II

|  | Thickness (micron) | Permeability (LMH/psi) | Mean flow bubble point for IPA (psi) | Nominal pore size rating (micron) | Porosity (%) | B. Diminuta LRV |
|---|---|---|---|---|---|---|
| Example 2: Nylon 225 | 225 | 1,814 | 33 | N/A | 90 | >9 |
| Example 2: Nylon 55 | 55 | 4,960 | 26 | N/A | 90 | >9 |
| Example 3: Nylon 55 | 160 | 3,354 | 13.7 | N/A | 90 | 5.5 |
| Comparative Example 2: Millipore Durapore ® GVPP | 125 | 500 | 30 | 0.22 | 75 | >9 |

A higher porosity of electrospun nanofiber mats results in greater permeability, while still providing a reliable means for retention of microorganisms.

Method of Use

Electrospun nanofiber containing liquid filtration media, in accordance with the present invention are useful in the food, beverage, pharmaceuticals, biotechnology, microelectronics, chemical processing, water treatment, an other liquid treatment industries.

Electrospun nanofiber containing liquid filtration media, in accordance with the present invention may be used for filtering, separating, identifying, and/or detecting microorganisms from a liquid sample or stream.

Electrospun nanofiber containing liquid filtration media, in accordance with the present invention may be used with any liquid sample preparation methods including, but not limited to, chromatography; high pressure liquid chromatography (HPLC); electrophoresis; gel filtration; sample centrifugation; on-line sample preparation; diagnostic kits testing; diagnostic testing; high throughput screening; affinity binding assays; purification of a liquid sample; size-based separation of the components of the fluid sample; physical properties based separation of the components of the fluid sample; chemical properties based separation of the components of the fluid sample; biological properties based separation of the components of the fluid sample; electrostatic properties based separation of the components of the fluid sample; and, combinations thereof. Also, electrospun nanofiber containing liquid filtration media, in accordance with the present invention can be component or part of a larger device and/or system.

Kits

The invention also provides kits which may be used to remove microorganisms from a liquid sample. The kit may comprise, for example, one or more electrospun nanofiber containing liquid filtration medium in accordance with the present invention, as well as one or more liquid filtration devices, support or substrate for the medium. The kit may contain one or more controls, and may optionally include various buffers useful in the methods of practicing the invention. Wash buffers for eliminating reagents or eliminating non-specifically retained or bound material may optionally be included in the kit.

Other optional kit reagents include an elution buffer. Each of the buffers may be provided in a separate container as a solution. Alternatively the buffers may be provided in dry form or as a powder and may be made up as a solution according to the user's desired application. In this case the buffers may be provided in packets. The kit may provide a power source in instances where the device is automated as well as a means of providing an external force such as a vacuum pump. The kit may also include instructions for using the electrospun nanofiber containing liquid filtration medium, device, support or substrate, and/or for making up reagents suitable for use with the invention, and methods of practicing invention. Optional software for recording and analyzing data obtained while practicing the methods of the invention or while using the device of the invention may also be included.

The term "kit" includes, for example, each of the components combined in a single package, the components individually packaged and sold together, or the components presented together in a catalog (e.g., on the same page or double-page spread in the catalog).

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

We claim:

1. A filtration device comprising a porous nanofiber containing filtration medium made by electrospinning a polymer, wherein the filtration medium exhibits full retention of *Brevundimonas diminuta* by size-based separation as measured in accordance with ASTM F838-83 and a liquid permeability greater than about 1000 LMH/psi, wherein the nanofiber has a fiber diameter from about 10 nm to about 1,000 nm.

2. The filtration device of claim 1, wherein the filtration medium has a thickness ranging from about 1 μm to about 500 μm.

3. The filtration device of claim 1, wherein the polymer is selected from the group consisting of polyimide, aliphatic polyamide, aromatic polyamide, polysulfone, cellulose acetate, polyether sulfone, polyurethane, poly(urea urethane), polybenzimidazole, polyetherimide, polyacrylonitrile, poly(ethylene terephthalate), polypropylene, polyaniline, poly(ethylene oxide), poly(ethylene naphthalate), poly (butylene terephthalate), styrene butadiene rubber, polystyrene, poly(vinyl chloride), poly(vinyl alcohol), poly (vinylidene fluoride), poly(vinyl butylene) and copolymers, derivative compounds, or blends thereof.

4. The filtration device of claim 1, wherein the polymer comprises an aliphatic polyamide.

5. The filtration device of claim 1, wherein the polymer comprises a blend of polymers or copolymers.

6. The filtration device of claim 1, wherein the electrospun nanofibers are disposed on a porous support.

7. The filtration device of claim 6, wherein the porous support comprises one or more layers selected from the group consisting of spunbonded nonwovens, meltblown nonwovens, needle punched nonwovens, spunlaced nonwovens, wet laid nonwovens, resin-bonded nonwovens, woven fabrics, knit fabrics, paper, and combinations thereof.

8. The filtration device of claim 1, wherein the filtration medium has a porosity from about 80% to about 95%.

9. The filtration device of claim 8, wherein the filtration medium has a thickness ranging from about 1 μm to about 500 μm.

10. The filtration device of claim 8, wherein the polymer is selected from the group consisting of polyimide, aliphatic polyamide, aromatic polyamide, polysulfone, cellulose acetate, polyether sulfone, polyurethane, poly(urea urethane), polybenzimidazole, polyetherimide, polyacrylonitrile, poly(ethylene terephthalate), polypropylene, polyaniline, poly(ethylene oxide), poly(ethylene naphthalate), poly(butylene terephthalate), styrene butadiene rubber, polystyrene, poly(vinyl chloride), poly(vinyl alcohol), poly(vinylidene fluoride), poly(vinyl butylene) and copolymers, derivative compounds, or blends thereof.

11. The filtration device of claim 8, wherein the polymer comprises an aliphatic polyamide.

12. The filtration device of claim 8, wherein the polymer comprises a blend of polymers or copolymers.

13. The filtration device of claim 8, wherein the nanofiber is disposed on a porous support.

14. The filtration device of claim 13, wherein the porous support comprises one or more layers selected from the group consisting of spunbonded nonwovens, meltblown nonwovens, needle punched nonwovens, spunlaced nonwovens, wet laid nonwovens, resin-bonded nonwovens, woven fabrics, knit fabrics, paper, and combinations thereof.

15. The filtration device of claim 8, wherein the porosity is about 90%.

16. The filtration device of claim 8, wherein the filtration medium is a multilayer porous nanofiber containing filtration medium.

17. The filtration device of claim 16, wherein the filtration medium has a thickness ranging from about 1 μm to about 500 μm.

18. The filtration device of claim 16, wherein the electrospun nanofibers are disposed on a porous support.

19. The filtration device of claim 18, wherein the porous support comprises one or more layers selected from the group consisting of spunbonded nonwovens, meltblown nonwovens, needle punched nonwovens, spunlaced nonwovens, wet laid nonwovens, resin-bonded nonwovens, woven fabrics, knit fabrics, paper, and combinations thereof.

20. The filtration device of claim 16, wherein the filtration medium has a porosity from about 80% to about 95%.

* * * * *